United States Patent [19]  [11] 4,146,554
Leigh  [45] Mar. 27, 1979

[54] PREPARATION OF CYANOESTERS

[75] Inventor: Thomas Leigh, Alderley Edge, England

[73] Assignee: Imperial Chemical Industries Limited, London, England

[21] Appl. No.: 803,236

[22] Filed: Jun. 3, 1977

[30] Foreign Application Priority Data

Jun. 16, 1976 [GB] United Kingdom ............... 24929/76
Jun. 16, 1976 [GB] United Kingdom ............... 24930/76

[51] Int. Cl.$^2$ .................. C07C 120/10; C07C 120/12
[52] U.S. Cl. ........................... 260/465 D; 260/559 R; 260/559 D; 424/304; 560/60; 560/105; 560/124; 562/470

[58] Field of Search .................. 260/465 D; 424/304

[56] References Cited

U.S. PATENT DOCUMENTS

| 2,387,435 | 10/1945 | Fleysher | 260/465 B |
| 3,317,585 | 5/1967 | Herschmann | 260/465.2 |
| 4,024,163 | 5/1977 | Elliott et al. | 260/465 D X |

Primary Examiner—Dolph H. Torrence
Attorney, Agent, or Firm—Cushman, Darby & Cushman

[57] ABSTRACT

A process for the preparation of certain cyano substituted esters and optical isomers thereof useful as insecticides by dehydration of the precursor carboxamido esters.

6 Claims, No Drawings

PREPARATION OF CYANOESTERS

This invention relates to a process for the preparation of certain cyano substituted esters useful as insecticides, and to certain novel isomeric forms of such esters produced thereby.

Elliott et al (Nature (1974), 248, 710) has reported the isolation of the insecticide (S)-α-cyano-3-phenoxybenzyl(IR, cis)-3-(2,2-dibromovinyl)-2,2-dimethylcyclopropane carboxylate, by crystallisation from the mixture of the two diastereoisomers which were obtained by esterifying (IR, cis)-3-(2,2-dibromovinyl)-2,2-dimethylcyclopropane carboxylic acid with racemic α-cyano-3-phenoxybenzyl alcohol. The corresponding mixture of dichlorovinyl compounds has been prepared (Elliot et al, Pesticide Sci (1975), 6, 537) but the constituent corresponding to the above dibromovinyl compound has not been isolated. It may be inferred that this dichlorovinyl derivative will also be a very potent insecticide. It is desirable therefore to prepare the isolated individual dichlorovinyl diastereoisomers viz (S)-α-cyano and (R)-α-cyano-3-phenoxybenzyl(IR, cis)-3-(2,2-dichlorovinyl)-2,2-dimethylcyclopropane carboxylates for evaluation as insecticides.

A preliminary examination of the mixture of diastereoisomers, an oil, indicated that separation by physical methods might be difficult. Obviously the most direct method for the production of the two isomers would be to esterify the cyclopropane carboxylic acid with the two enantiomers of α-cyano-3-phenoxybenzyl alcohol. Of the latter the (R) form has been prepared by Elliott et al (Nature (1974), 248, 710) by asymmetric addition of hydrogen cyanide to 3-phenoxybenzaldehyde in the presence of the enzyme D-oxynitrilase. Resolution of a cyanhydrin by the usual resolution techniques, for example via a diastereoisomeric precursor, has not been achieved. It is likely that the conditions necessary for the liberation of the cyanhydrin from a diastereoisomeric precursor will also racemise the cyanhydrin. Optically active benzaldehyde cyanhydrin, for example, is known to racemise under extremely mild conditions.

However methods involving enzyme treatment even if effective on the small scale are not really suitable for manufacture. We have therefore devised an alternative technique, utilising novel carboxamidoesters which does not rely upon enzyme treatments.

According to the present invention a process for the preparation of a compound of formula:

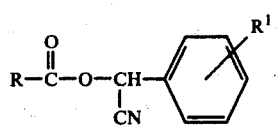

wherein R represents either (a) a group of formula:

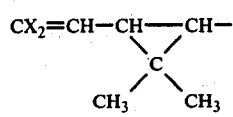

where X is chlorine, bromine or methyl, or (b) a group of formula:

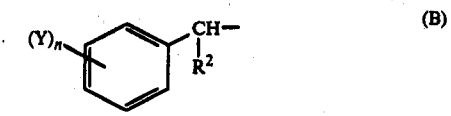

where Y is chlorine or methyl and n is one or two, and $R^2$ is an alkyl group containing from 2 to 4 carbon atoms; and $R^1$ is a phenoxy or 2,2-dichlorovinyloxy group; comprises the step of treating a compound of formula:

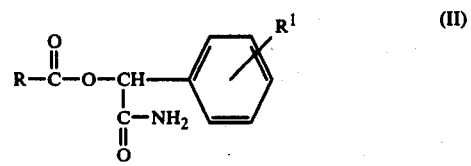

with a dehydrating agent.

A useful dehydrating agent is a phosphorus oxyhalide, for example, phosphorus oxychloride, and the process step is conveniently carried out by bringing a solution of the oxyhalide in a suitable solvent, for example a chlorinated hydrocarbon solvent such as methylene dichloride, into contact for a period of from about 30 minutes to about 30 hours with a solution of the compound of Formula II in a suitable solvent such as for example pyridine, at a temperature within the range −20° to +50° C., preferably within the range −10° to about +20° C.

It will be appreciated by those skilled in the art that in the compounds of Formula I the carbon atom to which the cyano atom is attached is substituted by four different groups or atoms and the compounds will show optical isomerism, as will the compounds of Formula II. The invention process may be used to convert racemates of Formula II to the racemate of Formula I, or it may equally well be used to convert compounds of Formula II in the (R)- or (S)-configuration to the corresponding isomers of the compounds of Formula I whilst retaining the stereochemical configuration around the optically active centre. That is the conversion from carboxamido to cyano occurs without racemisation or inversion or loss of optical purity. Thus the process is extremely useful in preparing individual stereochemical isomers of the compounds of Formula I.

Thus for example (S)-α-cyano-3-phenoxybenzyl (1R,3R)-3-(2,2-dichlorovinyl)-2,2-dimethylcyclopropane carboxylate may be prepared from (S)-α-carboxamido-3-phenoxybenzyl (1R,3R)-3-(2,2-dichlorovinyl)-2,2-dimethyl-cyclopropane carboxylate.

Other compounds which may be prepared by the invention process include the following:
(S)-α-cyano-3-phenoxybenzyl (1R,3R)-3-(2,2-dibromovinyl)-2,2-dimethylcyclopropane carboxylate,
(S)-α-cyano-3-(2,2-dichlorovinyloxy)benzyl (1R,3R)-3-(3,3-dichlorovinyl)-2,2-dimethylcyclopropane carboxylate,
(S)-α-cyano-3-phenoxybenzyl (1R,3R)-chrysanthemate,
(S)-α-cyano-3-phenoxybenzyl (+)-2-(4-chlorophenyl)isovalerate, and
(S)-α-cyano-3-(2,2-dichlorovinyloxy)benzyl (+)-2-(4-chloro-phenyl)isovalerate,
together with the corresponding (R)-α-cyano compounds.

The preparation of the compounds of Formula II is fully set out in our copending U.K. patent application No. 24931/76 entitled "Carboxamidoesters", and is also set out herein.

Particular compounds which are typical examples of compounds of Formula II include the following:

(+)-α-carboxamido-3-phenoxybenzyl (+)cis-trans-3-(2,2-dichlorovinyl)-2,2-dimethylcyclopropane carboxylate,
(S)-α-carboxamido-3-phenoxybenzyl (1R,3R)-3-(2,2-dichlorovinyl)-2,2-dimethylcyclopropane carboxylate, (S)-α-carboxamido-3-(2,2-dichlorovinyloxy)benzyl (1R,3R)-3-(2,2-dichlorovinyl)-2,2-dimethylcyclopropane carboxylate,
(+)-α-carboxamido-3-phenoxybenzyl (+)-(4-chlorophenyl)isovalerate,
(S)-α-carboxamido-3-phenoxybenzyl (+)-(4-chlorophenyl)isovalerate,
(S)-α-carboxamido-3-phenoxybenzyl (1R,3R)-3-(2,2-dibromovinyl)-2,2-dimethylcyclopropane carboxylate.

The compounds of Formula II may be prepared by reacting a compound of formula:

(III)

where Q is halogen, preferably chlorine, with an alcohol of formula:

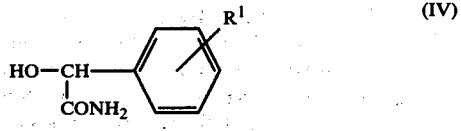

(IV)

optionally in the presence of a base.

Conveniently the above process may be performed by dissolving the alcohol of Formula IV in a suitable solvent in the presence of a base, or the solvent itself may be the base (e.g. pyridine) and adding to the solution a solution of the acid halide of Formula III in a suitable solvent, for example a hydrocarbon solvent, such as benzene or toluene, at a temperature within the range −5° to +30° C., preferably the ambient temperature. Although the reaction may be accelerated or completed by the application of heat, it is often sufficient merely to allow the reaction to proceed at the ambient temperature. The product may be isolated and purified by conventional techniques.

Alternative processes for the preparation of the esters of the invention include for example reaction of the acid of formula:

(V)

(optionally in the form of its salt) with a halide of formula:

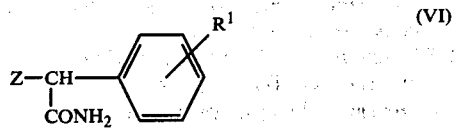

(VI)

or reaction of the acid of Formula V with the alcohol of Formula IV in the presence of a suitable acid catalyst.

Optically active compounds of Formula II may be prepared by reacting together optically active compounds of Formulae III or V with optically active compounds of Formulae IV or VI as appropriate, or by reaction of one optically active compound with a racemate of the other reactant followed by separation of the diastereoisomeric isomers by differential solubility e.g. by fractional crystallisation.

Thus, reaction of the (S)-isomer of an alcohol of Formula IV with the racemic form of a compound of Formula III (e.g. the (+)-cis-form of a compound of Formula III where R is a group of Formula A) to give a pair of diastereoisomers, which for convenience could be termed (+) (S) and (−) (S), and these could be separated by the use of fractional crystallisation techniques.

The alcohols of Formula IV are themselves novel compounds.

Compounds of formula:

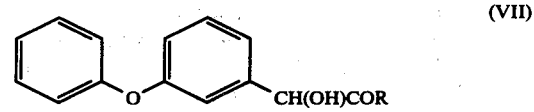

(VII)

wherein R is hydroxy, amino or alkoxy containing from 1 to 4 carbon atoms, and ammonium salts of such compounds wherein R is hydroxy, are particularly useful as intermediates in the preparation of the carboxamidoesters of Formula II.

Examples of specific compounds useful as intermediates include:
racemic 3-phenoxymandelic acid,
(S)-3-phenoxymandelic acid,
(R)-3-phenoxymandelic acid,
racemic 3-phenoxymandelamide,
(S)-3-phenoxymandelamide,
(R)-3-phenoxymandelamide,
racemic methyl 3-phenoxymandelate,
methyl (S)-3-phenoxymandelate,
methyl (R)-3-phenoxymandelate,
and examples of ammonium salts include the l-(−)-α-methylbenzylammonium and the d-(+)-α-methylbenzylammonium salts of racemic, (R)- and (S)-3-phenoxymandelic acids.

The compound of formula VII wherein R is OH may be obtained by the hydrolysis of 3-phenoxybenzaldehyde cyanhydrin, and it may be resolved into its constituent (R) and (S)-isomers by conversion to the salt of an optically active amine, for example α-methylbenzylamine. The salts may then be separated by their differential solubility characteristic e.g. by fractional crystallisation.

The hydrolysis of the cyanhydrin is preferably carried out using acid conditions, for example by heating the cyanhydrin with a dilute mineral acid in aqueous alcoholic solution for a period of from about 30 minutes to several hours. The process may be carried out using for example aqueous ethanolic hydrochloric acid at a temperature within the range 65° to 90° C., and may be supplemented by a period of treating the reactants with aqueous caustic alkali solution at a similar temperature. When the hydrolysis is complete the acid obtained may be purified by making a suitable water soluble salt, for example the sodium salt, to separate the acid from water insoluble material, and reprecipitating at pH less than 7 by using a mineral acid.

The compounds of formula VII wherein R is alkoxy as defined may be obtained for example by treating the 3-phenoxymandelic acid with an appropriate alcohol in the presence of an acid catalyst. This process may be conducted at the ambient temperature using for example an excess of the alcohol containing dissolved hydrogen chloride. Alternatively other methods of esterification may be used such as treating the alcohol with 3-phenoxy-mandelic acid halide in the presence of a base.

The compounds of formula VII wherein R is amino may conveniently be prepared by treating the alkyl esters of 3-phenoxymandelic acid with ammonia under pressure, for example by adding the ester to liquid ammonia at low temperature, and allowing the mixture to warm up to the ambient temperature in a sealed vessel.

The above processes may be used in sequence to convert 3-phenoxybenzaldehyde cyanhydrin to 3-phenoxy-mandelamide, and this latter compound either as the racemate or as the (R)- or (S)-isomer can be used for example in the preparation of α-carboxamido-3-phenoxybenzyl-3-(2,2-dihalovinyl)-3,3-dimethylcyclopropane carboxylates, which are themselves precursors for the insecticidally active α-cyano-3-phenoxybenzyl 3-(2,2-dihalovinyl)-3,3-dimethylcyclopropane carboxylates.

In a further aspect the invention relates to isolated fully resolved isomeric forms of an ester of 3-(2,2-dichlorovinyl)-2,2-dimethylcyclopropane carboxylic acid.

The substance α-cyano-3-phenoxybenzyl 3-(2,2-dichlorovinyl)-2,2-dimethylcyclopropane carboxylate possesses three asymmetrically substituted carbon atoms in its structure and can therefore theoretically exist in eight different isomeric forms. None of these forms has yet been described in isolation, although certain mixtures have been described in U.K. Patent specification No. 1,413,491.

The invention process involving dehydration of the precursor carboxamido esters allows each of these isomeric forms to be prepared in a substantially optically pure state.

Accordingly this invention provides in isolation in a substantially optically pure state each of the isomers of the compound α-cyano-3-phenoxybenzyl 3-(2,2-dichloro-vinyl)-2,2-dimethylcyclopropane carboxylate, that is -

(S)-α-cyano-3-phenoxybenzyl (1R,3S)-3-(2,2-dichlorovinyl)-2,2-dimethylcyclopropane carboxylate (Compound IX), (R)-α-cyano-3-phenoxybenzyl (1R,3S)-3-(2,2-dichlorovinyl)-2,2-dimethylcyclopropane carboxylate, (S)-α-cyano-3-phenoxybenzyl (1S,3R)-3-(2,2-dichlorovinyl)-2,2-methylcyclopropane carboxylate, (R)-α-cyano-3-phenoxybenzyl (1S,3R)-3-(2,2-dichlorovinyl)-2,2-dimethylcyclopropane carboxylate, (S)-α-cyano-3-phenoxybenzyl (1R,3R)-3-(2,2-dichlorovinyl)-2,2-dimethylcyclopropane carboxylate, (R)-α-cyano-3-phenoxybenzyl (1R,3R)-3-(2,2-dichlorovinyl)-2,2-dimethylcyclopropane carboxylate, (S)-α-cyano-3-phenoxybenzyl (1S,3S)-3-(2,2-dichlorovinyl)-2,2-dimethylcyclopropane carboxylate, (R)-α-cyano-3-phenoxybenzyl (1S,3S)-3-(2,2-dichlorovinyl)-2,2-dimethylcyclopropane carboxylate.

As set out hereinabove the method of preparing the compounds involves the dehydration of the corresponding α-carboxamido derivatives of Formula II. Thus, for example, Compound I can be prepared from the exact stereochemically equivalent α-carboxamido compound, that is, (S)-α-carboxamido-3-phenoxybenzyl (1R,3R)-3-(2,2-dichlorovinyl)-2,2-dimethylcyclopropane carboxylate.

The value of this process lies in the fact that (a) there is no change or loss of optical activity through inversion or racemisation and, (b) the diastereoisomeric forms of the α-carboxamido intermediates are solids and are easily separated by their differential solubility characteristics (in contrast to the known mixtures of the α-cyano isomers which are liquids) by for example frictional crystallisation techniques.

The individual isolated isomers of the invention have insecticidal properties, but each isomer has its own spectrum of activity and some isomers are intrinsically more active than others, and more active than the non-resolved material. Thus Compound IX is several times more active than the known (+)-α-cyano-3-phenoxybenzyl (+)-(50:50/cis-trans)-3-(2,2-dichlorovinyl)-2,2-dimethylcyclopropane carboxylate. It is interesting that the activity of the isomers in isolation is not necessarily in direct proportional relationship to their activity when present in the non-resolved material. This raises the possibility of actually mixing two or more of the isolated isomers together in various proportions to obtain a material with a particular insecticidal action, and could lead to the development of highly specific insecticidal preparations which would not affect non-target organisms adversely.

As stated above the individual isomers of Formula I are useful as insecticides, and are most conveniently used as such when formulated into compositions. In another aspect therefore the invention provides insecticidal compositions which comprise as an active ingredient an isomer of the compound α-cyano-3-phenoxybenzyl 3-(2,2-dichlorovinyl)-2,2-dimethylcyclopropane carboxylate, in a substantially optically pure state, in association with agriculturally and horticulturally acceptable diluent or carrier materials.

In a preferment of this aspect of the invention the active ingredient is (S)-α-cyano-3-phenoxybenzyl (1R,3R)-3-(2,2-dichlorovinyl)-2,2-dimethylcyclopropane carboxylate.

The compositions are for use in agriculture or horticulture but the type of composition used in any instance will depend upon the particular purpose for which it is to be used.

The compositions may be in the form of granules or powders comprising the active ingredient and a solid diluent or carrier. The compositions may also be in the form of liquid preparations to be used as dips or sprays which are generally aqueous dispersions or emulsions.

The compositions to be used as sprays may also be in the form of aerosols wherein the formulation is held in a container under pressure in the presence of a propellant such as fluorotrichloromethane or dichlorodifluoromethane.

For agricultural or horticultural purposes, an aqueous preparation containing between 0.0001% and 1.0% by weight of the active ingredient or ingredients may be used.

The compositions of the present invention may, if desired, also comprise in addition to an isomer of the present invention, at least one other biologically active ingredient, for example, an insecticide or a fungicide. They may also comprise a synergist of the type useful in synergising the activity of pyrethroids type insecticides.

In use, the invention compounds or compositions may be used to combat insects in a variety of ways. Thus the insects themselves, or the locus of the insects or the habitat of the insects is treated with a compound or a composition according to the invention.

The invention also provides a method of treating plants to render them less susceptible to damage by insects, which comprises treating the plants, or the seeds, corms, bulbs, tubers, rhizomes or other propagative parts of the plants, or the medium in which the plants are growing with an isomer or insecticidal composition according to the invention.

Thus the compounds of the invention are toxic towards a wide variety of insect and other invertebrate pests, including for example the following:

| | |
|---|---|
| Tetranychus telarius | Blattella germanica |
| Aphis fabae | Musca domestica |
| Megoura viceae | Pieris brassicae |
| Aedes aegypti | Plutella maculipennis |

The invention is illustrated by the following Examples, in which Examples 1 to 8 illustrate the preparation of intermediates and Example 9 illustrates the dehydration of the intermediate carboxamidoester to the corresponding nitrile.

EXAMPLE 1

This Example illustrates the preparation of racemic 3-phenoxymandelic acid.

A mixture of 3-phenoxybenzaldehyde cyanhydrin (208 g), ethanol (600 ml) and concentrated hydrochloric acid (400 ml) was kept at the ambient temperature for 24 hours, after which it was concentrated by evaporation under reduced pressure. 2N Sodium hydroxide solution (500 ml) was added to the residue and the mixture heated at 80° C. for one hour, cooled, concentrated hydrochloric acid (250 ml) added to it, and the resultant mixture heated at 80° C. for a further hour. The volatile portion was removed by evaporation under reduced pressure and the residue stirred with a solution of sodium bicarbonate (60 g) in water (60 g). The aqueous solution was decanted from the undissolved oil, stirred with activated charcoal, filtered, and the filtrate acidified with hydrochloric acid. The precipitated solid was collected by filtration and dried to yield racemic 3-phenoxymandelic acid, m.p. 131° C.

EXAMPLE 2

This Example illustrates the resolution of racemic 3-phenoxymandelic acid.

l-(−)-α-Methylbenzylamine (21.0 g) was added to a solution of racemic 3-phenoxymandelic acid (67.0 g) in isopropyl alcohol (700 ml) and the mixture kept for 24 hours at the ambient temperature. The solid precipitate was collected by filtration, (the filtrate kept — see below) and recrystallized twice from isopropyl alcohol (200 ml) to yield the l-(−)-α-methylbenzylammonium salt of (S)-3-phenoxymandelic acid, m.p. 153° C. This was then shaken with a mixture of diethyl ether (150 ml) and 5N hydrochloric acid (25 ml), the ether layer separated, washed with water, dried over anhydrous magnesium sulphate and concentrated by evaporation of the ether under reduced pressure to yield a residue of solid (S)-3-phenoxymandelic acid, m.p. 110°–112° C., $[\alpha]_D^{25}$ + 85° (C, 1.5, methanol).

The isopropyl alcohol solution obtained as a filtrate in the above process was concentrated by evaporation under reduced pressure until reduced to a volume of 50 ml. This was then shaken with 2N hydrochloric acid (150 ml) and the resultant solid precipitate collected by filtration. This solid (impure (R)-3-phenoxymandelic acid) was dissolved in isopropyl alcohol (400 ml) and d-(+)-α-methylbenzylamine (17.0 g) added to the solution. After keeping the mixture at the ambient temperature for a period of 24 hours the solid precipitate was collected by filtration, and recrystallised twice from isopropyl alcohol (200 ml) to yield the d-(+)-α-methylbenzyl-ammonium salt of (R)-3-phenoxymandelic acid, m.p. 154° C. Free (R)-3-phenoxymandelic acid was obtained from this salt by treatment in the manner described above for the isolation of the (S)-isomer. The (R)-isomer had m.p. 112° C., $[\alpha]_D^{25}$ −84° (C., 1.0, methanol).

EXAMPLE 3

This Example illustrates the preparation of (S)-3-phenoxymandelamide.

(S)-3-Phenoxymandelic acid (13.0 g) was added to a solution of dry hydrogen chloride (15.0 g) in methanol (100 ml) and the solution thus obtained kept at the ambient temperature for 24 hours after which period the volatile portion was evaporated yielding methyl (S)-3-phenoxymandelate as a residual oil. This was then added to liquid ammonia (20 ml) in a pressure vessel which was then sealed and temperature of the mixture allowed to rise to the ambient temperature over a period of 24 hours. The vessel was then opened and the excess of ammonia allowed to evaporate. The residual material was stirred with water and the solid collected by filtration, and recrystallised from benzene (70 ml) to yield impure (S)-3-phenoxymandelamide, m.p. 93° C. $[\alpha]_D^{25}$ + 25.4° (C.,2.0, methanol), (approximately 80% optically pure).

Optically pure material was obtained using the following procedure:

A suspension of the impure (S)-3-phenoxymandelamide (7.5 g) in a mixture of benzene (150 ml) and n-butanol (6 ml) was stirred at 25° C. for 30 minutes. The undissolved solid was separated by filtration and the filtrate was evaporated. The residue was recrystallised from benzene to give optically pure (S)-3-phenoxymandelamide, m.p. 94° C., $[\alpha]_D^{25}$ + 30° (c, 2.0, methanol).

Further optically pure (S)-3-phenoxymandelate was obtained by repeating the above purification procedure using the undissolved solid separated from the benzene/n-butanol mixture.

EXAMPLE 4

By using a procedure similar to that illustrated in the previous Example, (R)-3-phenoxymandelamide, m.p. 94° C., $[\alpha]_D^{25}$ −30° (c. 2, methanol) was obtained starting from (R)-3-phenoxymandelic acid, via the methyl ester and after final purification of the initially isolated 80% optically pure (R)-3-phenoxy-mendelamide, m.p. 93° C., $[\alpha]_D^{25}$ −25.3° (c. 2.0, methanol).

EXAMPLE 5

By using a procedure similar to that illustrated in the two previous Examples, racemic 3-phenoxymandelamide, m.p. 109° C., was obtained via racemic methyl 3-phenoxy-mandelate (m.p. 71° C.).

EXAMPLE 6

This Example illustrates the preparation of (S)-α-carboxamido-3-phenoxybenzyl (1R,3R)-3-(2,2-dichlorovinyl)-2,2-dimethylcyclopropane carboxylate.

A solution of (1R,3R)-3-(2,2-dichlorovinyl)-2,2-dimethylcyclopropane carboxylic acid chloride (0.45 g) in benzene (2.0 ml) is added at 5° C. to a solution of (S)-3-phenoxymandelamide (0.5 g) in pyridine (1.0 ml), and the mixture is kept at the ambient temperature for 24 hours. After this period the mixture is acidified with dilute hydrochloric acid, the benzene layer separated, washed with water and with aqueous sodium bicarbonate solution, dried and concentrated by evaporation of the benzene under reduced pressure. The residual oil is treated with cyclohexane (10 ml), and the precipitated solid collected by filtration and dried to yield (S)-α-carboxamido-3-phenoxybenzyl (1R,3R)-3-(2,2-dichlorovinyl)-2,2-dimethylcyclopropane carboxylate, m.p. 131° C.

EXAMPLE 7

This Example also illustrates the preparation of (S)-α-carboxamido-3-phenoxybenzyl (1R,3R)-3-(2,2-dichloro-vinyl)-2,2-dimethylcyclopropane carboxylate.

A solution of (1R,3R)-3-(2,2-dichlorovinyl)-2,2-dimethylcyclopropane carboxylic acid chloride (0.44 g) in benzene (2.0 ml) was added to a solution of racemic 3-phenoxymandelamide (0.5 g) in pyridine (1.0 ml) at 5° C. The mixture was kept for 24 hours at the ambient temperature and then acidified with dilute hydrochloric acid. The benzene layer was separated and washed with aqueous sodium bicarbonate solution. After concentration of the benzene solution by evaporation under reduced pressure to a volume of 1.0 ml, cyclohexane (3.0 ml) was added and the mixture kept at the ambient temperature. A solid (m.p. 124°) was precipitated on keeping, and this was collected by filtration and recrystallised from a mixture of benzene and cyclohexane to yield (S)-α-carboxamido-3-phenoxybenzyl (1R,3R)-3-(2,2-dichlorovinyl)-2,2-dimethylcyclopropane carboxylate, m.p. 131° C., identical with the product obtained in the previous Example.

The benzene/cyclohexane mother liquors contained impure (R)-α-carboxamido-3-phenoxybenzyl (1R,3R)-3-(2,2-dichlorovinyl)-2,2-dimethylcyclopropane carboxylate.

EXAMPLE 8

The procedure of the previous Example was used to prepare (S)-α-carboxamido-3-phenoxybenzyl (1R,3R)-3-(2,2-dichlorovinyl)-2,2-dimethylcyclopropane carboxylate, m.p. 131° C., identical with the product obtained in the previous Example, from racemic cis-3-(2,2-dichlorovinyl)-2,2-dimethylcyclopropane carboxylic acid chloride (0.65 g) and (S)-3-phenoxymandelamide (0.5 g). The benzene/cyclohexane mother liquors contained impure (S)-α-carboxamido 3-phenoxybenzyl (1S,3R)-3-(2,2-dichlorovinyl)-2,2-dimethylcyclopropane carboxylate.

EXAMPLE 9

This Example illustrates the preparation of (S)-α-cyano-3-phenoxybenzyl (1R,3R)-3-(2,2-dichlorovinyl)-2,2-dimethylcyclopropane carboxylate.

A solution of phosphorus oxychloride (0.33 g) in methylene dichloride (1.0 ml) was added dropwise over a period of 5 minutes to a solution of (S)-α-carboxamido-3-phenoxybenzyl (1R,3R)-3-(2,2-dichlorovinyl)-2,2-dimethylcyclopropane carboxylate (0.5 g) in pyridine (1.5 ml) whilst the temperature was maintained at −5° C. The mixture was then stirred at 0° C. for one hour, after which it was diluted with benzene and poured into dilute hydrochloric acid. The benzene layer was separated, washed with water and with aqueous sodium bicarbonate solution, dried and concentrated by evaporation of the benzene to yield a residue of (S)-α-cyano-3-phenoxybenzyl (1R,3R)-3-(2,2-dichlorovinyl)-2,2-dimethylcyclopropane carboxylate, m.p. 54° C., which on recrystallization from petroleum ether gave the pure material m.p. 57° C.

EXAMPLE 10

This Example illustrates the improved insecticidal properties of the isomer (S)-α-cyano-3-phenoxybenzyl (1R,3R)-3-)2,2-dichlorovinyl)-2,2-dimethylcyclopropane carboxylate (Compound IX) in comparison with the unresolved (+)-α-cyano-3-phenoxybenzyl (+)cis-trans-3-(2,2-dichlorovinyl)-2,2-dimethylcyclopropane carboxylate (containing about 40% cis and 60% trans material — Compound X).

Mustard plants are grown in pots until they reach the 7 to 8 leaf stage and then sprayed with aqueous compositions of the chemicals under test using a hand held spray gun operated at 15 psig. The plants are sprayed to maximum retention (just prior to run off) the spray being directed to both the upper and lower surfaces of the leaves. The aqueous compositions are prepared by dissolving the active ingredient in a small amount of acetone and mixing the solution with water to which 0.1% of an emulsifying agent ('Lissapol NX') has been added. ('Lissapol' is a Trade Mark).

When dry the plants are transferred to a constant environment chamber in which the temperature is maintained at 25° C. and relative humidity at 50%. Day length is controlled at 16 hours by the use of mercury vapour lamps. For each treatment a leaf is removed from the plant and placed on filter paper in a loosely covered petri dish (9 cm diameter) and infested with five half grown larvae of either *Plutella xylostella* or *Phaedon cochleariae*. Leaves are so removed and infested at intervals of zero, one, two, three and seven days, and assessed for mortality of the larval after 72 hours. Three replicates are used in each test.

The following Tables indicate the results obtained.

| COMPOUND | RATE PARTS/MILLION | % MORTALITY DAYS AFTER TREATMENT | | | | | PEST SPECIES |
|---|---|---|---|---|---|---|---|
| | | 0 | 1 | 2 | 3 | 7 | |
| IX | 3.9 | 100 | 93 | 80 | 20 | 53 | *Plutella* |
|  | 1.9 | 53 | 73 | 40 | 13 | 13 | *xylostella* |
| X | 3.9 | 67 | 80 | 33 | 0 | 0 | |
|  | 1.9 | 33 | 27 | 25 | 27 | 7 | |
| IX | 3.9 | 93 | 93 | 80 | 87 | 53 | *Phaedon* |
|  | 1.9 | 80 | 33 | 60 | 7 | 53 | *cochleariae* |
| X | 3.9 | 27 | 27 | 40 | 7 | 53 | |

| COMPOUND | RATE PARTS/MILLION | % MORTALITY DAYS AFTER TREATMENT | | | | | PEST SPECIES |
|---|---|---|---|---|---|---|---|
| | | 0 | 1 | 2 | 3 | 7 | |
| | 1.9 | 13 | 0 | 0 | 7 | 13 | |

The results clearly show that at equivalent rates the isolated isomer IX is considerably more active as an insecticides than the double racemate mixture of cis and trans isomers, represented by Compound X.

I claim:

1. A process for the preparation of a compound of formula:

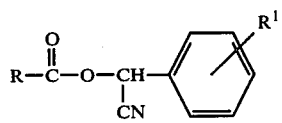 (I)

wherein R represents either (a) a group of formula:

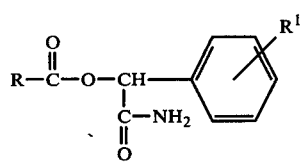 (A)

where X is chlorine, bromine or methyl, or (b) a group of formula:

 (B)

where Y is chlorine or methyl and n is one or two, and $R^2$ is an alkyl group containing from 2 to 4 carbon atoms; and $R^1$ is a phenoxy or 2,2-dichlorovinyloxy group; comprises the step of treating a compound of formula:

(II)

with a dehydrating agent at a temperature from about $-10°$ to about $+20°$ C.

2. A process as claimed in claim 1 in which the dehydrating agent is a phosphorus oxyhalide.
3. A process as claimed in claim 2 in which the phosphorus oxyhalide is phosphorus oxychloride.
4. A process as claimed in claim 1 carried out in the presence of a liquid diluent material.
5. A process as claimed in claim 4 in which the liquid diluent material includes pyridine.
6. A process as claimed in claim 4 in which the liquid diluent material includes a chlorinated hydrocarbon solvent.

* * * * *